US00RE44920E

(19) United States
(12) Reissued Patent
Dunn et al.

(10) Patent Number: US RE44,920 E
(45) Date of Reissued Patent: Jun. 3, 2014

(54) HIGH VOLUME LIQUID WASTE COLLECTION AND DISPOSAL SYSTEM

(71) Applicant: Dornoch Medical Systems, Inc., Riverside, MO (US)

(72) Inventors: James L. Dunn, Topeka, KS (US); Lawrence E. Guerra, Mission, KS (US)

(73) Assignee: Dornoch Medical Systems, Inc., Riverside, MO (US)

(21) Appl. No.: 13/772,686

(22) Filed: Feb. 21, 2013

Related U.S. Patent Documents

Reissue of:
(64) Patent No.: 7,892,420
Issued: Feb. 22, 2011
Appl. No.: 11/352,859
Filed: Feb. 13, 2006

U.S. Applications:
(63) Continuation-in-part of application No. 10/910,332, filed on Aug. 3, 2004, now Pat. No. 7,258,711.

(51) Int. Cl.
*C02F 1/00* (2006.01)
*A61M 1/00* (2006.01)

(52) U.S. Cl.
USPC ..... 210/96.1; 210/85; 210/143; 210/167.3; 210/198.1; 210/205; 210/241; 604/317

(58) Field of Classification Search
USPC ..... 210/743, 756, 765, 96.1, 143, 167.3, 210/198.1, 205, 241; 604/317
See application file for complete search history.

(56) References Cited

U.S. PATENT DOCUMENTS

| | | | |
|---|---|---|---|
| 4,224,154 | A | 9/1980 | Steininger |
| 5,776,260 | A | 7/1998 | Dunn et al. |
| 5,901,717 | A | 5/1999 | Dunn et al. |
| 5,975,096 | A | 11/1999 | Dunn et al. |
| 6,180,000 | B1 | 1/2001 | Wilbur et al. |
| 6,263,887 | B1 | 7/2001 | Dunn |
| 6,588,436 | B2 | 7/2003 | Dunn et al. |
| 6,672,477 | B2 | 1/2004 | Miller et al. |

(Continued)

OTHER PUBLICATIONS

"EHF Update—Disinfection and Disposal of Tissue Culture Waste", Dec. 14, 2004, Office of Environmental Health and Safety, Cornell University Medical College.*

*Primary Examiner* — Nam X. Nguyen
*Assistant Examiner* — Paul J Durand
(74) *Attorney, Agent, or Firm* — Seager, Tufte & Wickhem, LLC

(57) ABSTRACT

A system for collecting, treating and disposing of waste fluid includes a station that features transfer, flushing and mixing pumps as well as a bowl that holds the waste fluid. The waste fluid is collected in a container mounted on a cart. The cart container connects to the station so that the waste fluid is transferred from the cart to the station bowl by the transfer pump. The flushing pump has an inlet that communicates with a source of water and a disinfectant dispenser. The flushing pump is used to flush both the cart container and the station bowl, the latter of which communicates with a drain system. The flushing pump also delivers disinfectant to the waste fluid in the station bowl. The inlet and outlet of the mixing pump communicate with the bowl so that it mixes the bowl contents. Buffer is provided to the circulating waste fluid until the pH level drops to a predetermined level.

41 Claims, 10 Drawing Sheets

(56) References Cited

U.S. PATENT DOCUMENTS

| | | | |
|---|---|---|---|
| 6,776,175 | B2 | 8/2004 | Dunn et al. |
| 6,796,317 | B2 | 9/2004 | Dunn et al. |
| 6,893,425 | B2 | 5/2005 | Dunn et al. |
| 7,090,663 | B2 | 8/2006 | Dunn et al. |
| 7,258,711 | B2 | 8/2007 | Dunn et al. |
| 7,621,898 | B2 | 11/2009 | Lalomia et al. |
| 7,879,228 | B2 | 2/2011 | Dunn et al. |
| 7,892,420 | B2 | 2/2011 | Dunn et al. |
| 8,292,857 | B2 | 10/2012 | Martini et al. |
| 2003/0164600 | A1 | 9/2003 | Dunn et al. |
| 2005/0004537 | A1 | 1/2005 | Dunn et al. |
| 2005/0010179 | A1 | 1/2005 | Dunn et al. |

* cited by examiner

LOW/GRAV
FULL OPEN
CLOSED
OPEN
CLOSED
12
14
16
18a
18b
22
24
26b
32a
32b
34a
34b
36
42
44
54a
54b
55
56a
56b
58a
58b
62a
62b
64a
64b
72
106
120a
120b
124
146
154
168b
172
3

HIGH VOLUME LIQUID WASTE COLLECTION AND DISPOSAL SYSTEM

Matter enclosed in heavy brackets [ ] appears in the original patent but forms no part of this reissue specification; matter printed in italics indicates the additions made by reissue.

CROSS-REFERENCE TO RELATED APPLICATION

This application is a continuation-in-part of U.S. application Ser. No. 10/910,332, filed Aug. 3, 2004, which issued as U.S. Pat. No. 7,258,711.

BACKGROUND OF THE INVENTION

I. Field of the Invention

The present invention relates generally to systems for handling biological fluids and, in particular, to a system for collecting a large volume of liquid waste and safely disposing of the waste.

II. Description of the Related Art

Various forms of liquid medical wastes are commonly produced in surgery and other medical procedures. Such wastes may include blood and other body fluids of patients. The wastes may also include solid particles such as fragments of bone or cartilage. Some procedures produce a high volume of such waste from a single patient. For example, saline solution is used to irrigate the knee area during arthroscopic procedures. As another example, saline solution is used to flush the bladder, urethra and/or prostate in some urology procedures. Such procedures may produce as much as 30,000 cc of liquid medical waste.

Liquid medical waste generates significant disposal problems due to its possible contamination with various infectious diseases, including AIDS, hepatitis and MRSA. As a result, rules and regulations for the handling and disposal of liquid medical waste have been imposed by various governmental and regulatory agencies. For example, new regulations require the use of engineering controls to protect employees from exposure. In addition, hospitals and other health care facilities have been searching for methods and systems that reduce hospital personnel's exposure to the fluids during collection, handling and disposal. Procedures that produce large volumes of liquid medical waste amplify these issues and concerns.

Various systems and methods have been used for collecting, handling and disposing of fluids from procedures that produce large volumes of liquid medical waste. The collection vessels vary from simple buckets to automated, electronically controlled processing equipment.

A bucket, referred to as a "gravity bucket", may be placed by an operating room table or placed in another convenient location within the room in which a medical procedure is being performed. Flexible tubing typically connects the gravity bucket with the region of the patient from which the fluid wastes are collected. When the gravity bucket becomes filled, it is carried out of the operating room and its contents are poured down a drain. Such an arrangement has several drawbacks. Carrying the open bucket and emptying it manually creates the opportunity for direct human contact with the potentially infected wastes if the fluid spills or leaks from the bucket. In addition, the fluids may splash back or otherwise result in the formation of aerosols that contact the person disposing of the waste.

Suction canisters are commonly used to aspirate fluids from patients during surgical procedures. Such canisters range in volume from around 1200 cc to around 3000 cc. A suction canister typically features a removable lid with a vacuum port and a patient or suction port. During a surgical procedure, the vacuum port is connected by flexible tubing to a hospital vacuum source while the suction port is connected by a second flexible tube to the region of the patient from which the fluid wastes are collected.

As an alternative to a gravity bucket, a number of suction canisters may be positioned on a stand and connected in tandem. The stand features a base positioned on rollers so that the stand may be rolled to, from and around an operating room. A vertical rod extends upwards from the base and has a number of horizontal rings connected thereto. Each ring is sized to hold a suction canister and the rings are positioned on the vertical rod in a spaced and staggered fashion. The eight (for example) canisters positioned on the stand are connected in a tandem fashion as follows. The first canister has its suction port connected to the patient's surgery site by a flexible tube. The vacuum port of the first canister is connected to the suction port of a neighboring second canister. The vacuum port of the second canister is connected to the suction port of a third canister. The arrangement is repeated for the fourth through seventh canisters. The eighth canister suction port is connected to the vacuum port of the seventh canister while the vacuum port of the eighth canister is connected to the hospital vacuum source. As a result, each of the eight canisters is subjected to suction so that fluids produced by the medical procedure are collected in the canisters.

While such an arrangement allows a large volume of fluid to be collected, as the above description reveals, the connection of the canisters is complicated. If one mistake is made in connecting the tubing, no suction is available for the procedure. In addition, the stand becomes somewhat top heavy with the canisters filled so that the cart becomes difficult to maneuver and great care must be exercised when moving the cart. The arrangement also results in a large number of canisters to clean or dispose of as infectious waste. Using the above example, one procedure would result in eight canisters that need to be dumped and cleaned. This is very time consuming. The large number of canisters required also makes the arrangement expensive.

Systems for collecting and disposing of high volumes of fluids are offered by the Steris Corporation of Mentor, Ohio, as the "SafeCycle 40", and Stryker Instruments of Kalamazoo, Mich., as the "Neptune Waste Management System."

The Steris "SafeCycle 40" system, described in U.S. Pat. Nos. 4,863,446 and 4,957,491, both to Parker, is a fluid collection and disposal system featuring a mobile fluid collection cart and a disposal station. The fluid collection cart includes vacuum and suction ports that communicate with a reservoir that is positioned on the cart. The reservoir also features a drain outlet. A vacuum line connects the vacuum port of the collection cart to a hospital vacuum source during surgery so that fluid is withdrawn from the patient via flexible tubing that is connected to the cart's suction port and collected in the reservoir. The collection cart features a vacuum regulator that permits the level of suction provided by the cart suction ports to be adjusted by knobs on the cart. After surgery, the collection cart is connected to the disposal station via washing and draining connectors so that the reservoir is drained and flushed via a timed cleaning process.

The Stryker "Neptune" system, described in U.S. Pat. Nos. 5,997,733 and 6,180,000, both to Wilbur et al., is a portable waste disposal system that includes a waste collection system, a smoke extraction system and a treatment and disposal system that heats the waste to sanitize it for disposal. The system includes a container that features a vacuum port that is connected to a vacuum source of a hospital. The container also includes a suction port that is in communication with the patient surgery site via flexible tubing. As a result, fluids from the patient are collected in the container. Smoke is withdrawn from the patient surgery site by an additional flexible tube that is in communication with the head space of the container. The smoke is filtered as it is withdrawn from the head space into a housing that contains additional filters and a fan that pulls the smoke into the housing. The container also includes a drain which may either be connected to the treatment system or a hospital drain so that the fluid in the container may be drained or treated and then drained.

While the Steris and Stryker systems have proven to be effective, the systems are unable to accommodate suction canisters of the 1200 cc to 3000 cc variety. As a result, a separate cleaning and disposal system for the smaller suction canisters must be purchased by a hospital in addition to the Steris and Stryker machines. This results in an increase in purchase expenses and personnel training for a hospital or other health care facility. The requirement for two separate systems also results in increased maintenance costs. Due to their complexity, the Steris and Stryker systems are also quite costly. Also due to their complexity, at least in part, the carts of the Steris and Stryker systems are heavy when their containers are full. This makes pushing and maneuvering the carts burdensome.

Laboratories, manufacturing equipment and industrial processes may also produce biological wastes that must be conveniently and safely disposed of. For example, automated cell culture growing equipment in a pharmaceutical laboratory may empty the cell culture waste into an area that must be vacuumed out. A large volume of the cell culture waste fluid is collected during the vacuuming and must be disposed of.

Accordingly, it is an object of the present invention to provide a system for safely and conveniently collecting a large volume of waste fluid.

It is another object of the present invention to provide a system that permits large volumes of waste fluid to be treated and disposed of without contact by personnel.

It is still another object of the present invention to provide a system for collecting, treating and disposing of large volumes of waste fluid that is easy to configure and operate.

It is still another object of the present invention to provide a system that facilitates treating of large volumes of waste fluid.

Other objects and advantages will be apparent from the remaining portion of this specification.

SUMMARY OF THE INVENTION

A system for collecting, treating and disposing of waste fluid includes a waste fluid treating and disposing station featuring a housing having transfer and flushing connectors and a bowl. A flushing pump has an inlet in communication with a disinfectant dispenser and an outlet selectively in communication with the bowl and the flushing connector. A transfer pump has an inlet in communication with the transfer connector and an outlet in communication with the bowl. A mixing pump has an inlet and an outlet in communication with the bowl so that the waste fluid therein is circulated. A pH sensor is in communication with the bowl so that a pH level of the circulating waste fluid may be detected. A container holds a supply of buffer. A pH controller delivers buffer to the circulating waste fluid when the pH sensor detects that the pH level of the circulating waste fluid is above a predetermined pH level.

The system for collecting, treating and disposing of waste fluid may also feature a waste fluid collection cart including a body supported by wheels. A container is supported by the body and features vacuum, suction, flushing and drain ports. Liquid waste is collected within the container through the suction port when the vacuum port is connected to a vacuum source and the flushing and drain ports are closed. After waste fluid is collected in the cart, it is disconnected from the vacuum source and the drain port of the cart container is connected to the transfer connector of the station so that waste fluid from the cart container is transferred to the station bowl when the transfer pump is activated. The flushing port of the cart container is connected to the flushing connector of the station so that disinfectant may be directed to the cart container when the flushing pump is activated. Disinfectant is also directed to the station bowl when the outlet of the flushing pump is redirected to the bowl.

The following detailed description of embodiments of the invention, taken in conjunction with the appended claims and accompanying drawings, provide a more complete understanding of the nature and scope of the invention.

DETAILED DESCRIPTION OF THE INVENTION

Figure 1:
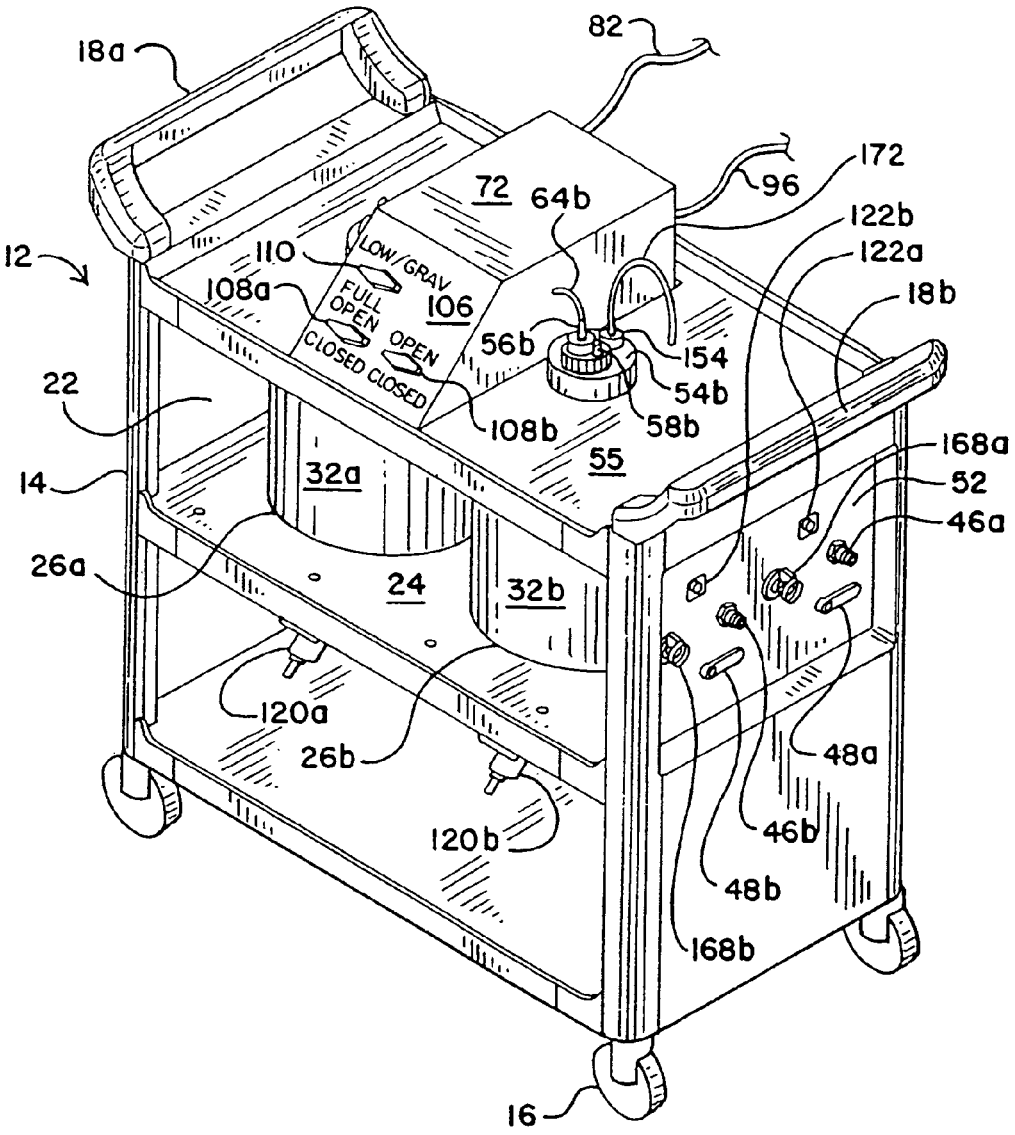
FIG. 1 is a perspective view of a fluid collection cart of an embodiment of the system of the present invention.
Figures 2, 3:
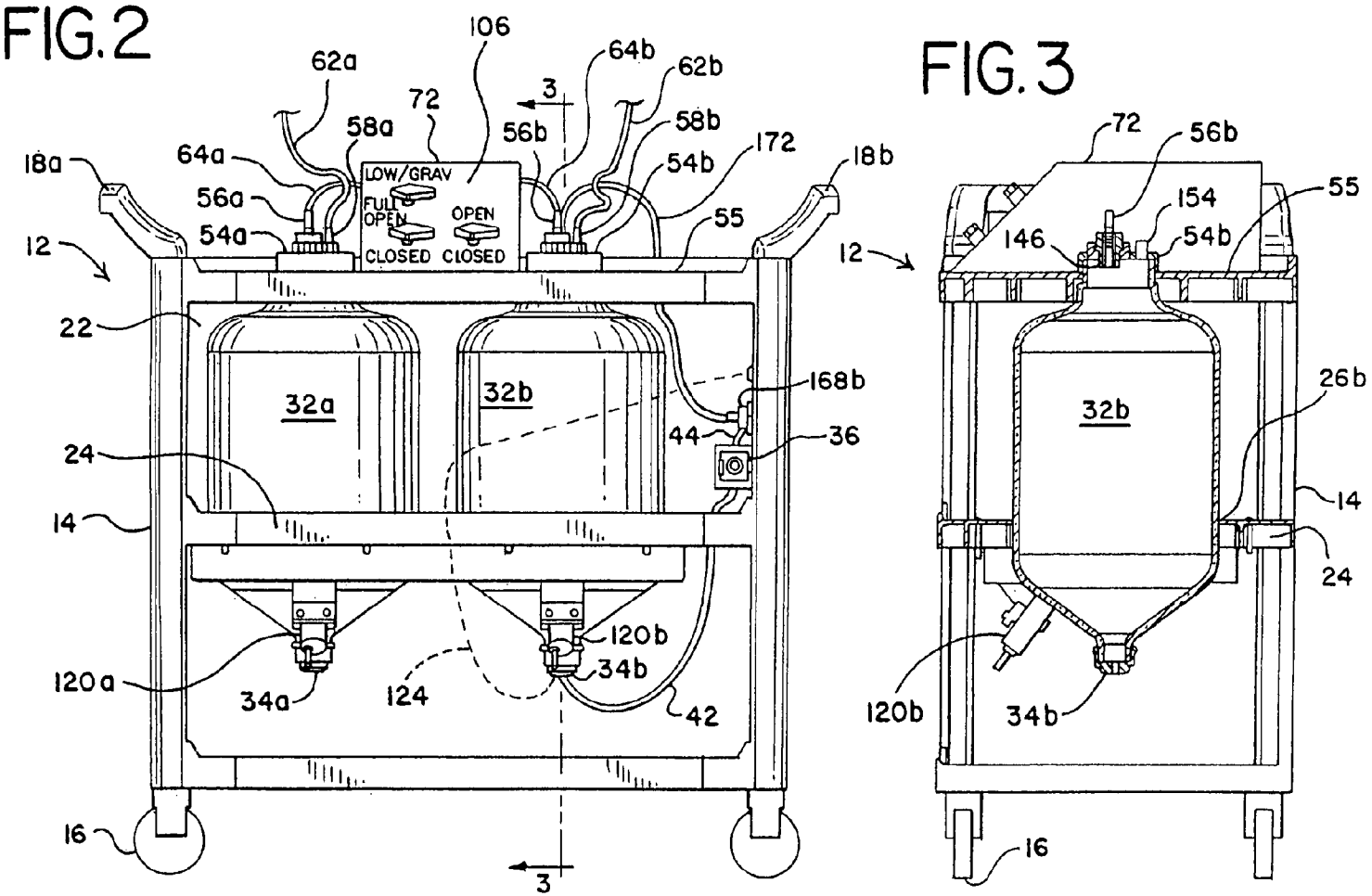
FIG. 2 is a side elevation view of the cart of FIG. 1.
FIG. 3 is a sectional view of the cart of FIG. 2 taken along line 3-3.

The fluid collection cart of a preferred embodiment of the system of the present invention is indicated in general at 12 in FIGS. 1-3. The cart features a cabinet-like body 14 that is supported at its bottom four corners by wheels 16. Opposing handles 18a and 18b are secured to the top of the cart body 14 to facilitate pushing, pulling and maneuvering of the cart. The cart 12 is preferably constructed of plastic for strength, durability and light weight.

The cart body 14 defines an interior space 22 within which a shelf 24 is mounted. While not illustrated, doors may optionally be provided on the cart so that the interior space 22 is hidden from view when the doors are closed. Shelf 24 features a pair of openings 26a and 26b formed therein within which bottle-shaped containers 32a and 32b are secured. Containers 32a and 32b are preferably constructed of glass for ease of cleaning and are sized to hold approximately six gallons of liquid each.

As illustrated in FIGS. 2 and 3, the bottom of each container 32a and 32b is provided with a drain port, 34a and 34b, respectively. As illustrated in FIG. 2, drain port 34b is connected to the inlet of a drain valve 36 by line 42. The outlet of drain valve 36 communicates by line 44 with a drain connector, illustrated at 46b in FIG. 1. Both drain valve 36 and drain connector 46b are mounted to a side panel 52 of cart 12. Drain valve 36 may be opened or closed by drain valve handle 48b. When drain valve 36 is closed, communication between the drain connector 46b and the drain port 34b of container 32b is prevented. When drain valve 36 is open, fluid within container 32b flows to drain connector 46b. Drain connector 46a is connected to drain port 34a of container 32a in a similar fashion through a valve (not shown) that is controlled by drain valve handle 48a. The associated tubing has been omitted from FIG. 2 for the sake of clarity. In addition, all tubing has been omitted from FIG. 3 for the sake of clarity. Drain valve handles 48a and 48b are configured so that their corresponding valves are closed when the cart is used during a medical procedure to collect biological fluids.

Figure 8:
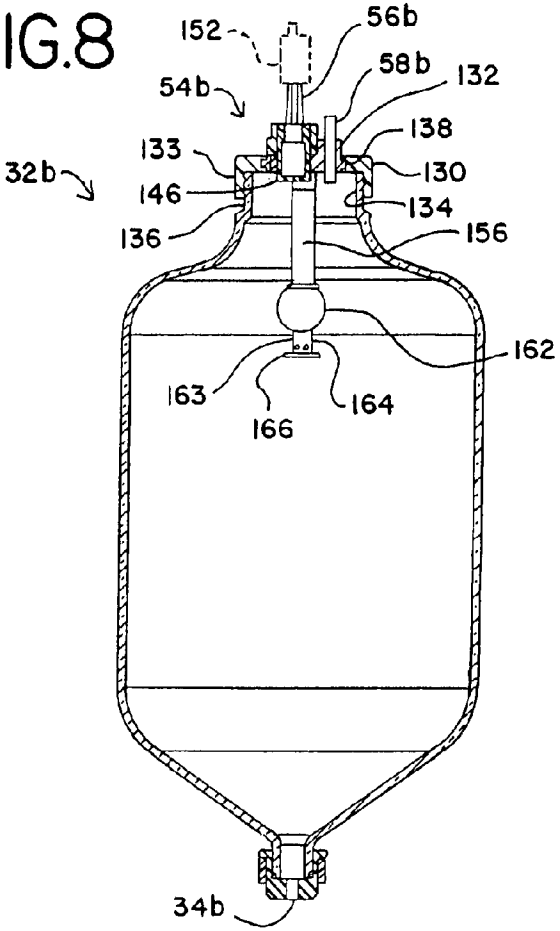
FIG. 8. is a sectional view of the container of FIG. 7 taken along line 8-8.

The tops of containers 32a and 32b are closed by caps 54a and 54b, respectively, which extend through the top surface 55 of cart body 14. Caps 54a and 54b preferably are constructed of plastic and feature vacuum ports 56a and 56b and patient or suction ports 58a and 58b. As illustrated in FIG. 2, the suction ports 58a and 58b are connected to flexible tubing suction lines 62a and 62b which lead to the region of the patient from which the fluid wastes are collected. Fluids are withdrawn from the patent via tubing 62a and 62b and collected in containers 32a and 32b, respectively, when vacuums are pulled on the containers via vacuum ports 56a and 56b. Vacuum ports 56a and 56b are connected via flexible tubing 64a and 64b, respectively, to a regulator housing 72 that is mounted upon the top surface 55 of the cart body 14. As illustrated in FIG. 8, the vacuum port is equipped with a Porex filter 146 that, in addition to filtering (as will be described below), may cooperate with the hospital vacuum source to automatically stop suction when the canister is full.

Figure 4:
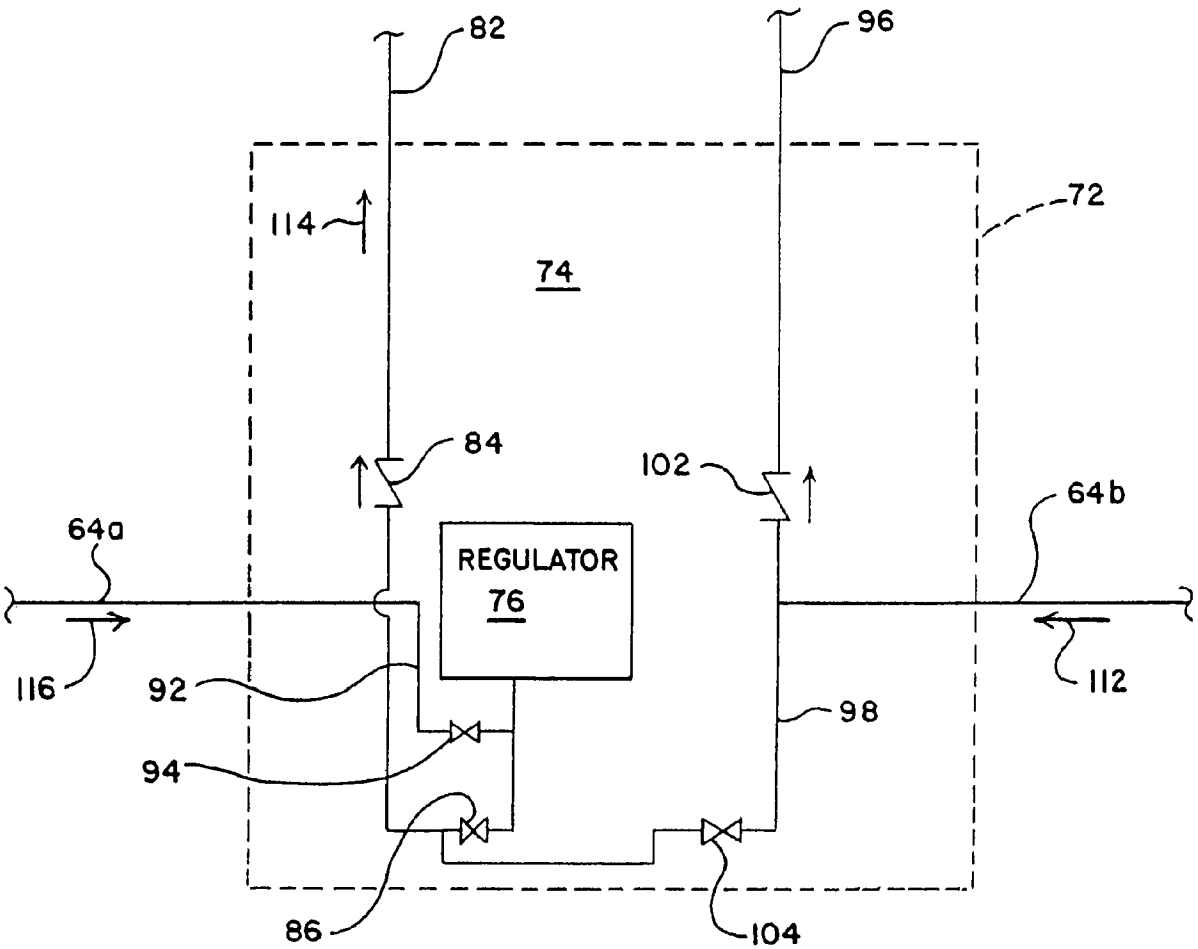
FIG. 4 is a schematic view of the regulator housing of the cart of FIGS. 1-3.

As illustrated in FIG. 4, housing 72 defines a chamber 74 that features a regulator 76 preferably set to 5 in. Hg and associated valves and piping. More specifically, line 64a leads to regulator 76. A vacuum source line 82 is connected to a hospital vacuum source and communicates with regulator 76 through check valve 84 and control valve 86. A bypass line 92 connects line 82 with line 64a through bypass valve 94. A second vacuum source line 96 may be placed in communication with a second hospital vacuum source and communicates with line 64b and crossover line 98 through check valve 102. Crossover line 98 is equipped with control valve 104 and communicates with hospital vacuum source line 82.

As illustrated in FIG. 1, housing 72 features a control panel 106 featuring valve handles 108a, 108b and 110. All three valve handles may be manipulated between two positions. Valve handles 108a and 108b may both be toggled between "open" and "closed" settings. Valve handle 110 may be toggled between "full" and "low/gravity drain" settings. Valve handle 108a configures control valve 86 of FIG. 4 between the open and closed positions, valve handle 108b configures control valve 104 of FIG. 4 between the open and closed positions and valve handle 110 configures control valve 94 of FIG. 4. The "full" setting of valve handle 110 corresponds to an open condition for bypass valve 94 and a "low/gravity drain" setting of valve handle 110 corresponds to a closed condition for bypass valve 94.

The operating mode of the cart during a medical procedure depends upon the configuration of valve handles 108a, 108b and 110 and whether one or both of vacuum source lines 82 and 96 are connected to hospital vacuum sources. Taking first the situation where only vacuum source line 82 is connected to a hospital vacuum source, a full vacuum of approximately 25 in. Hg is pulled on container 32b through lines 64b, 98 and 82, as illustrated by arrows 112 and 114, when valve 104 is opened (via valve handle 108b of FIG. 1).

With the cart connected to a single hospital vacuum source through line 82, and a full vacuum being pulled on container 32b, container 32a may simultaneously pull a low or gravity drain vacuum of approximately 5 in. Hg when valve handle 108a (FIG. 1) is placed in the "open" position, so that valve 86 is open, and valve handle 110 is placed in the "low/gravity drain" position so that bypass valve 94 is closed. With reference to FIG. 4, this results in a vacuum being pulled on line 64a, as illustrated by arrow 116, and thus container 32a, by line 82 through regulator 76 so that the vacuum pulled on line 64a and container 32a is limited by regulator 76 to 5 in. Hg. As a result, the system of the present invention provides for both high level suction and gravity drain via suction lines 62b and 62a (FIG. 2), simultaneously during a medical procedure.

If valve 104 is shut, by placing corresponding valve handle 108b of FIG. 1 in the "closed" position, no vacuum is pulled on container 32b and either a low vacuum of approximately 5 in. Hg or a high vacuum of approximately 25 in. Hg may be pulled on container 32a by toggling valve handle 110 between the "low/gravity drain" and "full" positions, respectively. With valve handle 110 set to the "full" position, bypass valve 94 is opened so that the vacuum pulled on line 64a, and thus canister 32a, by line 82 bypasses regulator 76. Of course, valve 86 must be open, with corresponding valve handle 108a of FIG. 1 placed in the "open" position.

If both lines 82 and 96 are connected to hospital vacuum sources, and valves 86, 104 and 94 are open, a full vacuum of approximately 25 in. Hg is pulled on each container 32a and 32b.

As illustrated at 120a and 120b in FIGS. 1-3, a liquid level detector is positioned on the bottom of each container 32a and 32b. While other devices known in the art may be used, liquid level detectors 120a and 120b preferably are capacitance sensors. As illustrated in FIG. 2, capacitance sensor 120b is connected to electrical connector 122b, shown mounted to the cart body side panel 52 in FIG. 1, by electrical line 124. Sensor 120a is connected to electrical connector 122a of FIG. 1 in a similar fashion, however, the corresponding electrical line has been omitted from FIG. 2 for the sake of clarity. As will be explained below, the sensors 120a and 120b and electrical connectors 122a and 122b, along with drain connectors 46a and 46b, find use during the draining and flushing or cleaning cycles.

Figure 6:
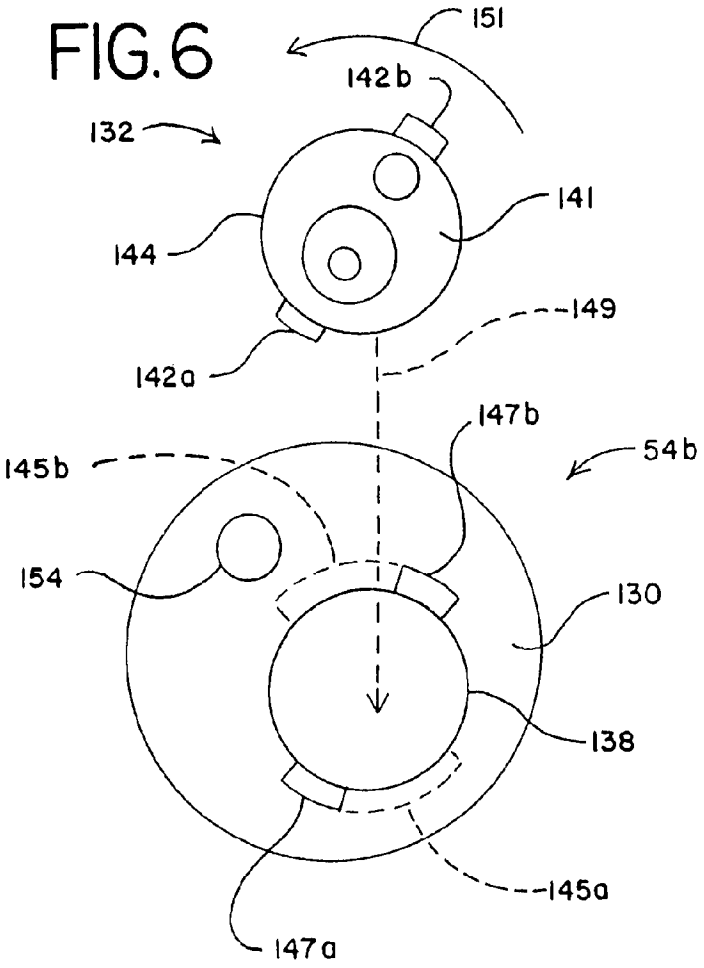
FIG. 6 is an exploded top plan view of the container cap of FIG. 5.
Figure 5:
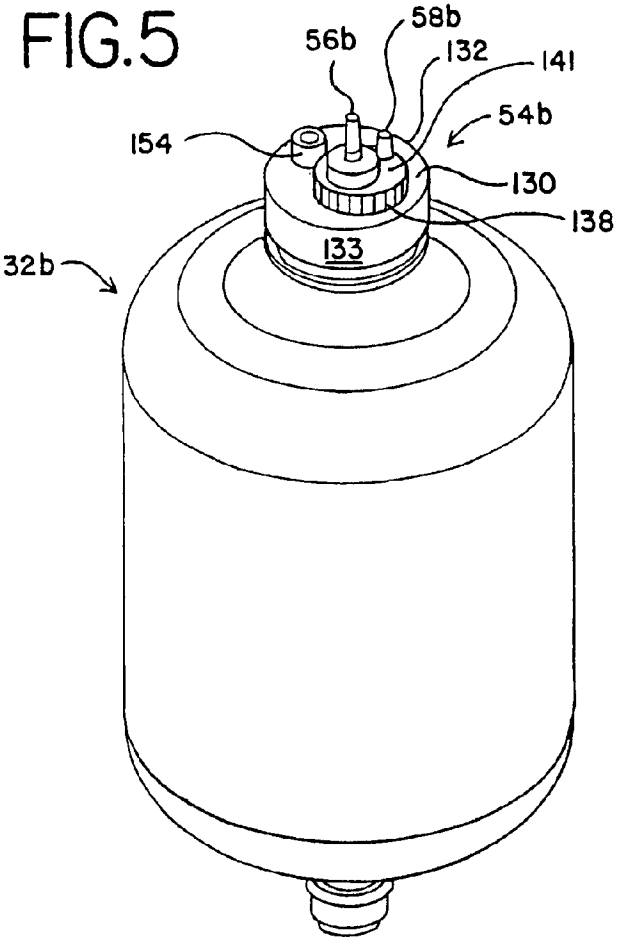
FIG. 5 is an enlarged perspective view of one of the containers of the cart of FIGS. 1-3.
Figure 7:
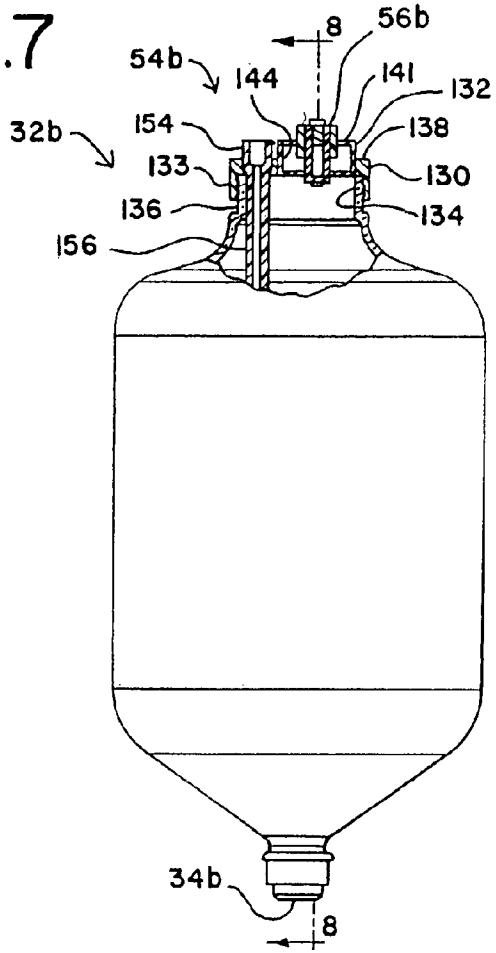
FIG. 7 is a partially broken-away side elevation view of the container of FIG. 5.

Enlarged and detailed views of container 32b are presented in FIGS. 5, 7 and 8. It is to be understood that container 32a features an identical construction. As illustrated in FIGS. 5-8, plastic cap 54b includes an outer portion 130 and an inner portion 132. As illustrated in FIGS. 7 and 8, the outer portion 130 of cap 54b features a downward extending skirt 133 with a threaded inner surface 134. The outer cap portion 130 screws onto the threaded top opening 136 of container 32b via threaded inner surface 134 and also features a bore 138.

The inner portion 132 of cap 54b features vacuum port 56b and patient or suction port 58b formed in its circular surface 141. In addition, as illustrated in FIG. 6, inner cap portion 132 has a pair of opposing tabs 142a and 142b formed on its circumference 144. Corresponding horizontal slots 145a and 145b are formed in the bore 138 of outer cap portion 130. A pair of vertical channels 147a and 147b corresponding to the width of the tabs are formed between the top surface of the outer cap portion 130 and the horizontal slots 145a and 145b. As a result, as indicated by dashed arrow 149 in FIG. 6, the tabs 142a and 142b of the inner cap portion 132 may be lowered via the vertical channels 147a and 147b into the horizontal slots 145a and 145b and turned in the direction indicated by arrow 151 so that the inner cap portion 132 is locked within the bore 138 of the outer cap portion 130.

As a result, inner cap portion 132 may be removed from the outer cap portion 130 for disposal after use. This is desirable in that potentially contaminated biological fluids from a medical procedure flow through suction port 58b during a medical procedure. In addition, as illustrated in FIG. 8, the vacuum port 56b is provided with a Porex filter 146. This prevents bacteria and fluids from entering the hospital vacuum source. It is thus desirable to dispose of the Porex filter after use. This is also accomplished by disposing of the inner cap portion 132.

It should be noted that other temporary inner cap portion fastening arrangements may be substituted for the one illustrated in FIG. 6. For example, bore 138 of outer cap portion 130 and the circumference 144 of inner cap portion 132 could be provided with mating threads so that the inner cap portion is screwed into the bore of the outer cap portion.

During a surgical procedure, the surgical site of a patient may undergo procedures that produce smoke. Examples of such procedures include cauterizing and drilling. Such smoke contains foul smelling and potentially infectious airborne particles. As a result, for sanitary reasons, such smoke must removed from the patient's surgical site. As illustrated in phantom at 152 in FIG. 8, a smoke plume filter may optionally be connected to vacuum port 56b so as to be in series with line 64b of FIGS. 1 and 2. Such filters are known in the art and permit the canister 32b to collect smoke from a patient's surgery site via suction tube 62b of FIG. 2. In order to accomplish this, full suction (approximately 25 in. Hg) must be pulled on canister 32b.

As illustrated in FIGS. 5-7, the outer cap portion 130 is equipped with a flushing port 154. As illustrated in FIG. 7, the flushing port 154 communicates with a conduit 156, preferably constructed of plastic, that extends down into the interior of container 32b. Positioned on the end of conduit 156 is a cleaning nozzle, illustrated at 162 in FIG. 8. Cleaning nozzle 162 preferably rotates when liquid is supplied thereto so that water and cleaning solution flowing to the nozzle is sprayed onto the interior surfaces of container 32b.

In some instances, the spray provided by nozzle 162 causes the pressure within container 32b to increase rapidly. The increased pressure within the container 32b causes liquid to back up in conduit 156, sometimes as high as six to eight inches. To combat this occurrence, a "top hat" shaped piece 163 may optionally be added to conduit 156 so as to extend below the nozzle 162. The top hat piece features a number of orifices 164 through which liquid from the conduit flows. The liquid then cascades over the brim 166 of the top hat piece. As a result, the pressure head within the container 32b is collapsed so that the back up of liquid into conduit 156 does not occur.

With reference to FIGS. 1 and 2, the flushing port 154 is connected to a flushing connector 168b via flexible tubing 172. The flushing port of the cap of container 32a is connected to the flushing connector 168a of FIG. 1 in a similar fashion. Both flushing connectors 168a and 168b are mounted to the side panel 52 of cart body 14. As with electrical connectors 122a and 122b and drain connectors 46a and 46b, the flushing connectors 168a and 168b find use during the draining and cleaning cycles which now will be described. The flushing connectors 168a and 168b feature integral valves that seal when the connectors are not connected to lines so that vacuums may be pulled within containers 32a and 32b during fluid collection.

After a medical procedure is completed, or the containers 32a and 32b are filled, lines 82 and 96 (FIG. 1) are disconnected from the hospital vacuum source(s) and suction lines 62a and 62b (FIG. 2) are disconnected from the suction ports 58a and 58b. Caps are then placed upon the suction ports and the cart is wheeled out of the operating room to a separate room containing the draining and cleaning station. As will be described below, a modified version of the "RedAway II" system sold by Dornoch Medical Systems, Inc. of Riverside, Mo. may be used as the draining and cleaning station for the cart. The RedAway II system is described in detail in U.S. Pat. No. 6,588,436, the contents of which are incorporated herein by reference.

Figure 9:
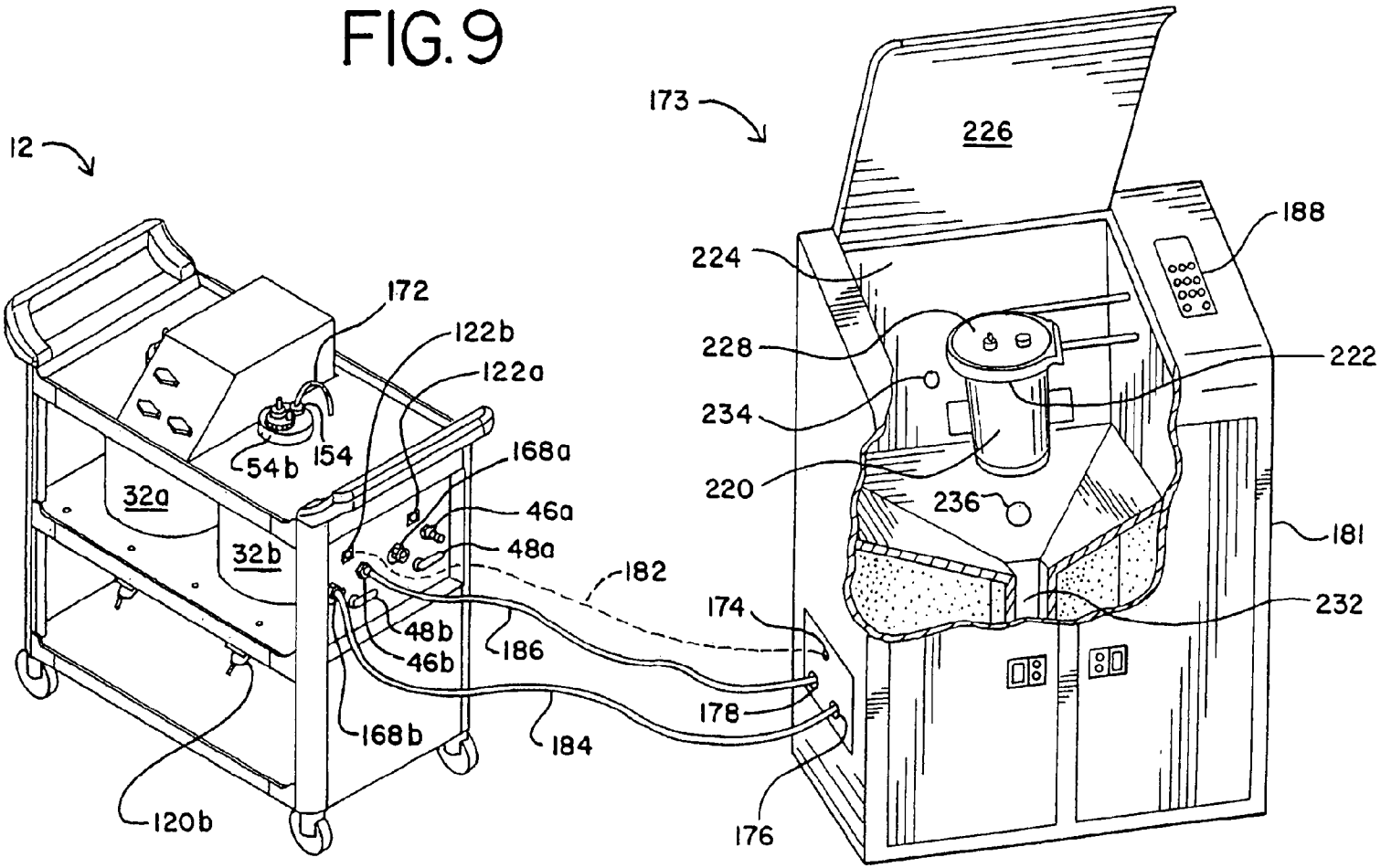
FIG. 9 is a partially broken-away perspective view of the cart of FIG. 1 connected to a draining and cleaning station.

FIG. 9 illustrates the cart 12 connected to the draining and cleaning station, indicated in general at 173, so that the container 32b of cart 12 may be drained and cleaned. Similar to cart 12, draining and cleaning station 173 features electrical, flushing and drain connectors, illustrated at 174, 176 and 178, respectively. As illustrated in FIG. 9, the electrical, flushing and drain connectors of the cart, 122b, 168b and 46b, are each connected to the corresponding connectors positioned on the housing 181 of cleaning station 173 by line 182 and flexible tubing 184 and 186, respectively. After these connections are made, drain valve handle 48b is opened. The entire draining and cleaning process may now be controlled from the control panel 188 of the station 173.

Figure 10:
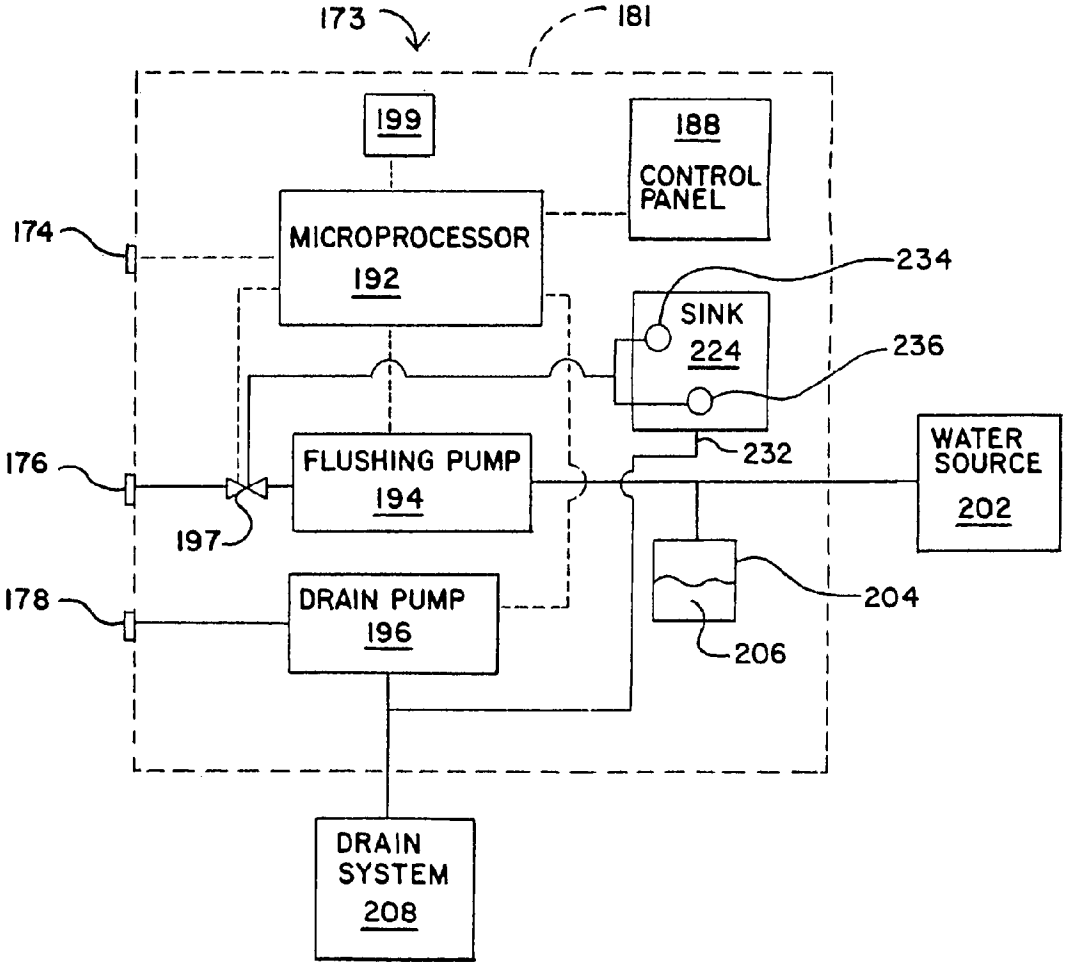
FIG. 10 is a schematic view of the draining and cleaning station of FIG. 9.

As illustrated in FIG. 10, the draining and cleaning station 173 includes a microprocessor 192 that communicates with capacitance sensor 120b via electrical connectors 174, 122b, line 182 and line 124 (FIG. 2). The microprocessor also communicates with the control panel 188 of the cleaning station as well as a drain pump 194 and a flushing pump 196. The flushing pump inlet is in communication with a water supply source 202. A dispenser 204 containing a supply of bleach 206, or other additive, is positioned within the draining and cleaning station cabinet 181 and also communicates with the water supply source 202 and the inlet of flushing pump 194. The drain pump communicates with the hospital or health care facility drainage system 208. The drain and flushing pumps 196 and 194 also communicate with the drain and flushing connectors 178 and 176.

Microprocessor 192 also communicates with an automated control valve 197. Control valve 197 may be configured to route the mixture of bleach and water from pump 194 to either flushing connector 176 or spray jets 234 and 236, which are positioned in the sink 224 of the station. The microprocessor also communicates with the draining and cleaning station canister handling mechanism 199. As will be explained below, these components permit the draining and cleaning station to drain and flush suction canisters and are disabled when the station is draining and flushing the containers of cart 12.

Figure 11:
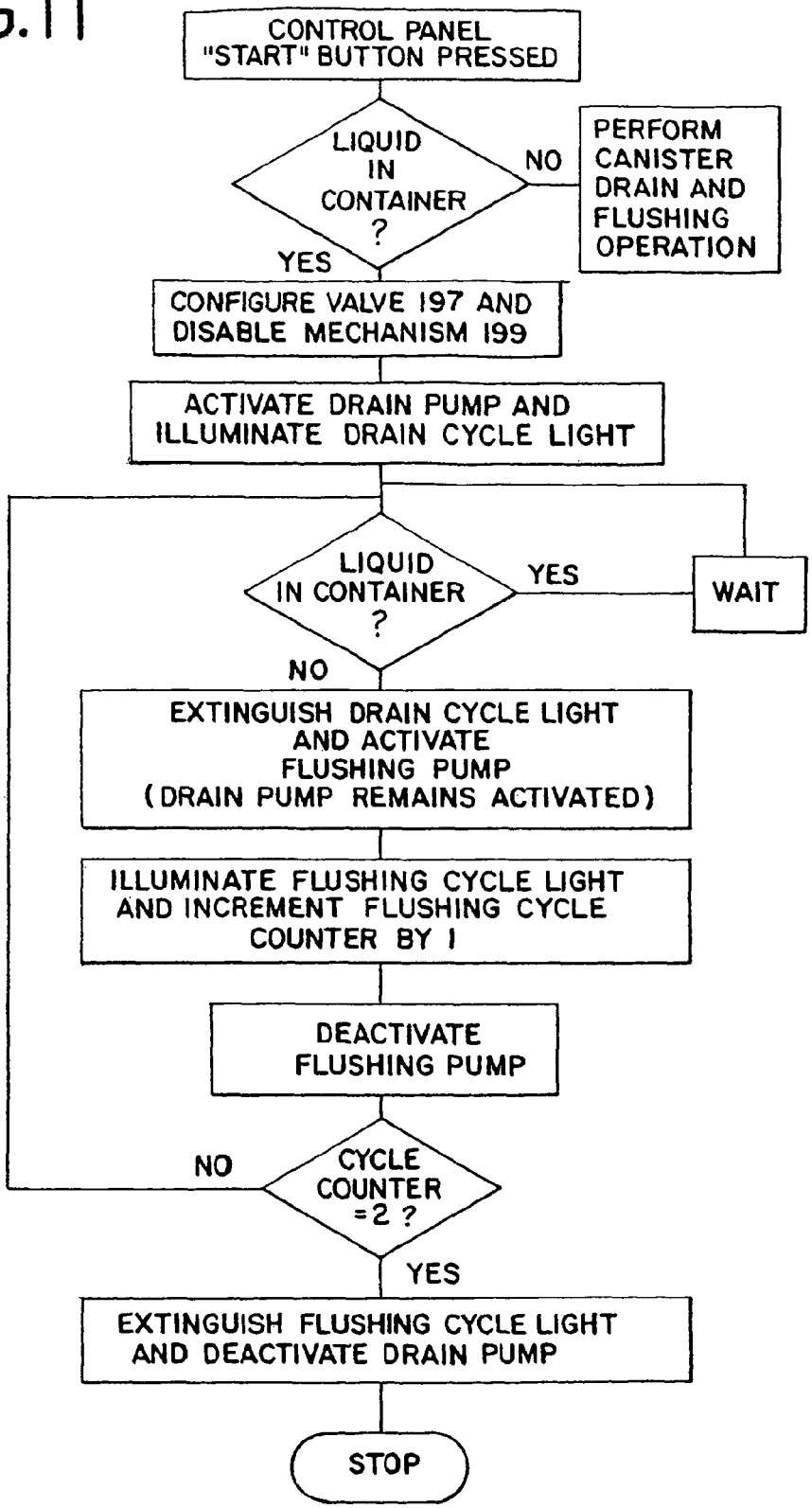
FIG. 11 is a flow diagram showing the steps of the software program of the microprocessor of FIG. 10.

The processing performed by the microprocessor 192 of FIG. 10 is illustrated in FIG. 11. When the draining cycle is initiated by a "start" button on control panel 188, the microprocessor first checks for the presence of liquid waste in container 32b via capacitance sensor 120b (FIGS. 1-3). If liquid waste is in container 32b, as will be discussed in greater detail below, the microprocessor reconfigures valve 197 and disables canister handling mechanism 199. The microprocessor also illuminates a "drain cycle" indicator light on the control panel 188 and activates drain pump 196 so that the contents of the container are drained through line 42 (FIG. 2), line 186 (FIG. 9) and directed to the drain system 208.

When the capacitance sensor 120b (FIGS. 1-3) indicates to the microprocessor that the liquid waste has been drained from the container, flushing pump 194 is activated. The "drain cycle" indicator light on panel 188 is also extinguished and a "flushing cycle" indicator light is illuminated. Flushing pump 194 sends a stream consisting of a mixture of water and bleach, from water source 202 and dispenser 204, respectively, through lines 184 and 172 (FIG. 9) to the flushing port 154 of the cap 54b of container 32b. As a result, the interior of container 32b is sprayed with the water and bleach mixture by the nozzle 162 of FIG. 8. Drain pump 196 remains activated so that the mixture of bleach, water and residue is withdrawn from the container and directed to drain system 208.

After a period of time, the flushing pump is deactivated. The drain pump continues to run so that all of the liquid in container 32b drains. When the capacitance sensor 120b indicates that the container is empty, the flushing pump is once again activated so that the flushing cycle is repeated. Microprocessor 192 keeps track of the number of flushing cycles performed by using, for example, the cycle counter included in FIG. 11. Preferably, two or three flushing cycles are performed. When the last flushing cycle is performed, the "flushing cycle" light on control panel 188 is extinguished and the drain pump is deactivated. The draining and flushing cycles are then completed. Container 32b is then prepared for reuse by the removal and disposal of the inner cap portion 132 (FIGS. 5-8). A new replacement inner cap portion 132 is then installed.

Once draining and flushing of container 32b is completed, the drain valve handle 48b is closed and the connectors 174, 176 and 178 of station 173 are disconnected from connectors 122b, 168b and 46b. The station connectors are then reconnected to cart connectors 122a, 168a and 46a and drain valve handle 48a is opened so that container 32a may be drained and flushed.

As described in U.S. Pat. No. 6,588,436, when cart 12 is not present, the draining and cleaning station may alternatively be used to clean suction canisters. With reference to FIG. 9, a filled canister 220 is placed within a bracket 222 which is secured within sink 224 which is positioned within the housing 181 of the station. After the lid 226 of the station is closed, and the "start" button on control panel 188 is pressed, the lid 228 of the canister is automatically removed and the canister is rotated about a horizontal axis by the canister handling mechanism (199 in FIG. 10). The contents of the canister then drain into the sink 224 and down drains 232 and 208 (FIGS. 9 and 10). Spray jets 234 and 236 then spray the inverted canister with a mixture of bleach and water (FIGS. 9 and 10). As illustrated in FIG. 11, when the capacitance sensor of cart 12 is connected to the draining and cleaning station 173, and the station "start" button is pressed, the microprocessor of the station recognizes the presence a filled cart container and reconfigures valve 197 of FIG. 10 so that liquid from the pump is directed to connector 176 and the canister handling mechanism 199 is also disabled so that the canister cleaning operation cannot be performed.

While FIGS. 9-11 are described with respect to the draining and cleaning station of U.S. Pat. No. 6,588,436, other canister draining and cleaning stations or systems may be easily modified to clean the containers of cart 12. These stations include those illustrated in U.S. Pat. Nos. 6,263,887 and 5,901,717, the latter of which is sold by Dornoch Medical Systems, Inc. as the "RedAway I" system. Both patents are also owned by Dornoch Medical Systems, Inc.

As an alternative to collecting medical waste, the cart 12 of FIGS. 1-3 and 9 may be used to collect fluid waste from a laboratory, manufacturing equipment or industrial process. For example, automated cell culture growing equipment in a pharmaceutical laboratory may empty the cell culture waste into an area that must be vacuumed out. The large volume of cell culture waste is collected in the containers 32a and 32b of cart 12 through the suction ports 58a and 58b. While the invention will be described below in terms of cell culture waste, it is to be understood that it could alternatively be used to collect, treat and dispose of other types of waste.

Figure 12:
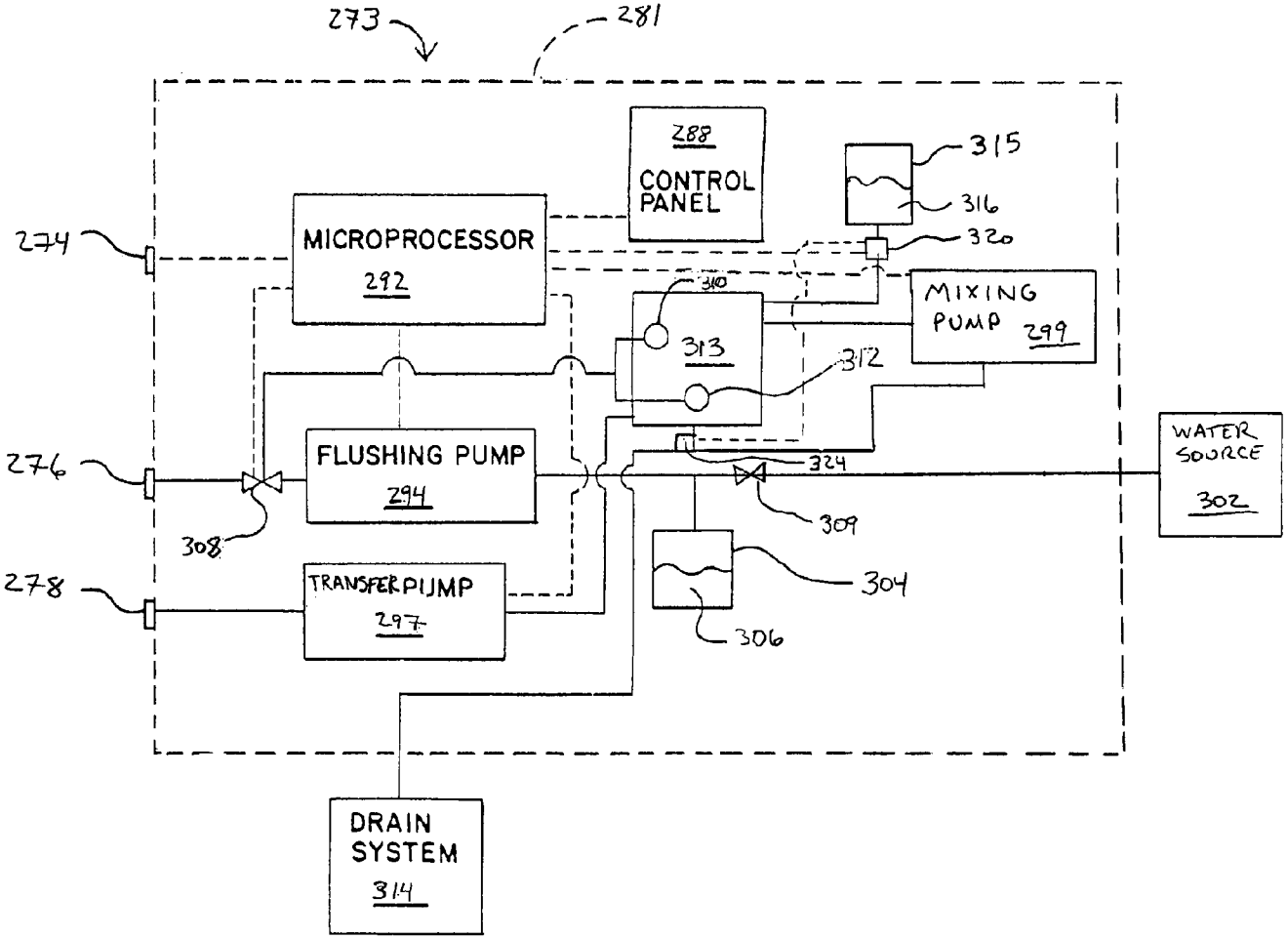
FIG. 12 is a schematic view of an embodiment of the waste fluid treating and disposing station of the present invention.

A draining and cleaning station suitable for receiving, treating and disposing of the cell culture waste fluid collected in cart 12 of FIGS. 1-3 and 9 is indicated in general at 273 in FIG. 12. Similar to the draining and cleaning station 173 of FIG. 9, draining and cleaning station 273 includes a housing, indicated in phantom at 281 in FIG. 12, and electrical, flushing and transfer connectors, illustrated at 274, 276 and 278, respectively. When it is desired to drain and flush container 32b of the cart, the electrical, flushing and drain connectors of the cart, 122b, 168b and 46b in FIG. 9, are connected to the electrical, flushing and transfer connectors 274, 276 and 278 of the station (FIG. 12), respectively, in the fashion illustrated by line 182 and flexible tubing 184 and 186 in FIG. 9. After these connections are made, drain valve handle 48b of the cart (FIG. 9) is opened. With reference to FIG. 12, the entire draining and cleaning process may now be controlled from the control panel 288 of the station 273.

Container 32a of the cart may alternatively be drained and flushed by connecting electrical, flushing and drain connectors of the cart, 122a, 168a and 46a (FIG. 9), to the electrical, flushing and transfer connectors 274, 276 and 278 of the station (FIG. 12) and opening drain valve handle 48a.

As illustrated in FIG. 12, the draining and cleaning station 273 includes a microprocessor 292 that communicates with the capacitance sensors of the cart (120a and 120b of FIGS. 1 and 2) via electrical connector 274. The microprocessor also communicates with the control panel 288 of the cleaning station as well as a flushing pump 294, a transfer pump 297 and a mixing pump 299.

The flushing pump inlet is in communication to a water supply source 302. A dispenser 304 containing a supply of bleach 306, or other disinfectant, is positioned within the draining and cleaning station cabinet 281 and also communicates with the water supply source 302 and the inlet of flushing pump 294. Microprocessor 292 also communicates with automated control valves 308 and 309. Control valve 308 may be configured to route the mixture of bleach and water from flushing pump 294 to either flushing connector 276 or wash heads 310 and 312, which are positioned in the tank or bowl 313 of the station. Valve 309 permits the delivery of either pure bleach or a mixture of bleach and water. The bowl 313 also communicates with a drain system 314, which will be described in better detail below with regard to FIG. 13.

The inlet of the transfer pump 297 communicates with transfer connector 278, while the outlet communicates with station bowl 313.

Both the inlet and outlet of mixing pump 299 communicate with the station bowl 313. A container 315 holding a supply of buffer 316 communicates with bowl 313 under the control of metered pH controller 320.

The station 273 may or may not have the capacity to also clean canisters. In the case of the former, the bowl 313 would be in the form of sink 224 described above with reference to FIGS. 9 and 10. The embodiment of the station described below, however, is assumed to not have the capacity to also clean canisters.

Figure 13:
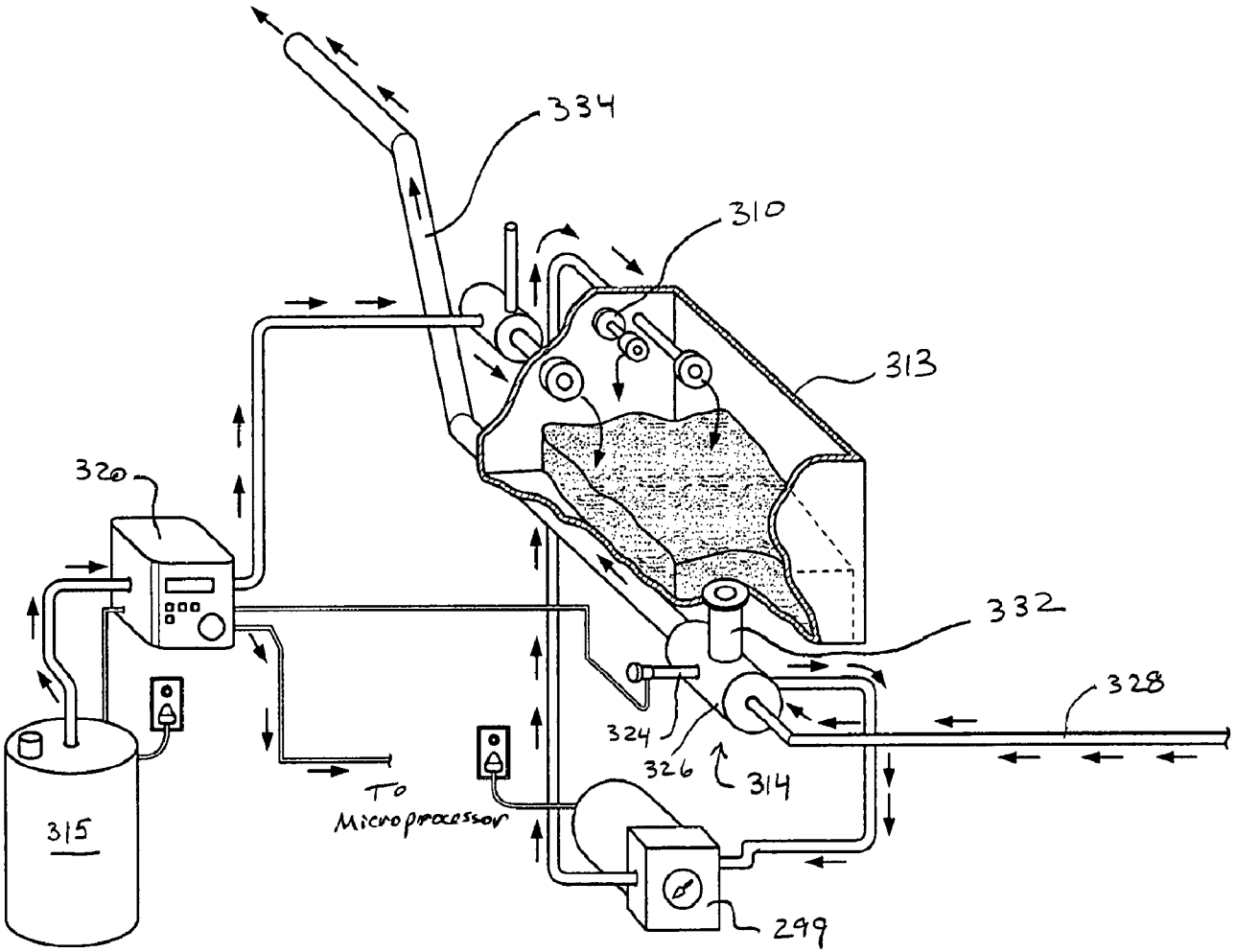
FIG. 13 is a perspective view of the primary components of the waste fluid treating and disposing station of FIG. 12.

Operation of the station 273 of FIG. 12 will now be explained with reference to FIGS. 12 and 13. One or both of the containers 32a and 32b of cart 12 (FIGS. 1-3 and 9) contain cell culture waste fluid. Operation of the invention is described below in terms of container 32b, but it should be understood that the contents of container 32a would be treated in a similar fashion.

When the "Wash" cycle is initiated by a button on the station control panel 288, the microprocessor 292 first checks for the presence of cell culture waste fluid in container 32b via capacitance sensor 120b (FIGS. 1-3). The microprocessor also configures valve 308 so that the outlet of flushing pump 294 communicates with wash heads 310 and 312 of bowl 313 and valve 309 so that pure bleach from dispenser 304 may be delivered to the wash heads. If waste fluid is in container 32b, the microprocessor simultaneously activates transfer pump 297 and flushing pump 294. As a result, the contents of the container 32b are transferred to station bowl 313 and pure bleach is added thereto through wash heads 310 and 312. The capacitance sensor 120b of the cart detects if the cart is more or less than half full, or equal to half full, so that the microprocessor can control the amount of bleach added to bowl 313. Bleach volume is preferably approximately 80 oz. if the cart is more than half full and 40 oz. if the cart is half full or less.

Mixing pump 299 is next activated so that the bleach and cell culture waste in the station bowl 313 is thoroughly mixed. The mixing may occur, for example, approximately 20 seconds. The mixed solution then preferably sits in the station bowl 313 for a hold time of approximately 10 minutes, or for another specified period of time as required by applicable standards and regulations.

At the end of the hold time period, the cart is washed. More specifically, the valves 308 and 309 are reconfigured to direct a water and bleach mixture to flushing connector 276. Flushing pump 294 is then activated by the microprocessor. Flushing pump 294 sends a stream consisting of a mixture of water and bleach from water source 302 and dispenser 304 to, with reference to FIG. 9, the flushing port 154 of the cap 54b of container 32b. As a result, the interior of container 32b is sprayed with the water and bleach mixture by the nozzle 162 of FIG. 8. Transfer pump 297 is activated so that the contents of container 32b are pumped to the station bowl 313.

Once the cart container 32b is completely emptied and the contents pumped into the station bowl 313, the mixing pump 299 and metered pH controller 320 are activated by microprocessor 292 and remain activated until the pH of the solution drops to a predetermined level. More specifically, as mixing pump 299 re-circulates the liquid from bowl 313, a pH sensor 324 detects and measures the pH of the solution. The pH sensor 324 communicates with the metered pH controller 320 so that when the pH is above the predetermined level (for example, 9), buffer is added to the station bowl, and thus the solution, from buffer container 315. As an example only, the buffer 316 may be a 1 Molar solution of Citric Acid.

It is to be understood that as an alternative to the illustrated embodiment where the pH controller 320 is a separate meter component, the pH controller may take the form of an automated valve in circuit between the buffer container 315 and the bowl 313, where the automated valve operates under the direction of the microprocessor 292. In such an embodiment, the pH sensor 324 communicates directly with the microprocessor 292.

Once the solution in the station bowl has a pH below the predetermined level (9 in the above example), the contents of the station bowl may be emptied via a drain system, indicated at 314 in FIG. 12 and in general at 314 in FIG. 13. As illustrated in FIG. 13, the drain system preferably includes an eductor 326 to facilitate and speed drainage of the station bowl. A flow of water enters the eductor 326 through inlet line 328 and flows through a venturi that communicates with drain pipe 332. The flow of water accelerates as it flows through the venturi which causes a pressure drop in drain pipe 332. As a result, fluid is withdrawn from station bowl 313 through drain pipe 332 by suction in addition to gravity. The treated waste is directed by the eductor and drain system 314 to the facility sewer system through treated waste discharge line 334. The valves 308 and 309 of FIG. 12 are reconfigured so that water is directed through wash heads 310 and 312 and sink 313 is rinsed. The eductor 326 (FIG. 13) remains running so that the resulting fluid is also directed to the sewer system.

While the preferred embodiments of the invention have been shown and described, it will be apparent to those skilled in the art that changes and modifications may be made therein without departing from the spirit of the invention, the scope of which is defined by the appended claims.

What is claimed is:

1. A station for treating waste fluid including:

a) a housing;

b) a [bowl] *reservoir* positioned within said housing and adapted to receive the waste fluid from a source and communicate with a drain system;

c) a mixing pump having an inlet and an outlet in communication with the [bowl] *reservoir* so that waste fluid therein is circulated;

d) a pH sensor in communication with the [bowl] *reservoir* so that a pH level of the circulating waste fluid may be detected;

e) a container holding a supply of buffer;

f) a pH controller in circuit between the buffer container and the [bowl] *reservoir* so that said pH controller controls the delivery of buffer to the circulating waste fluid;

g) said pH controller communicating with the pH sensor so that said pH controller delivers buffer to the circulating waste fluid when the pH sensor detects that the pH level of the circulating waste fluid is above a predetermined pH level;

h) a wash head positioned in the [bowl] *reservoir*;

i) a dispenser containing a disinfectant;

j) a flushing pump having an inlet in communication with a the disinfectant dispenser and an outlet in communication with the wash head so that when said flushing pump is activated, disinfectant is delivered to the contents of the [bowl] *reservoir*;

k) a transfer pump having an inlet in communication with a transfer connector and an outlet in communication with the [bowl] *reservoir*, said transfer connector adapted to communicate with the waste fluid source so that when said transfer pump is activated, waste fluid is transferred from the waste fluid source to the [bowl] *reservoir*; and l) a microprocessor in communication with the pH sensor and in communication with and controlling the pH controller, mixing pump, flushing pump and transfer pump.

2. The station of claim 1 wherein the waste fluid is cell culture waste fluid.

3. The station of claim 1 wherein the drain system includes drain pipe adapted to communicate with a sewer system and an eductor in communication with the drain pipe, said eductor including a venturi adapted to communicate with a water source so that water flows through the venturi which results in suction being applied to the drain pipe to aid in draining treated waste fluid from the station [bowl] *reservoir*.

4. The station of claim 1 wherein the pH controller includes an automated valve in circuit between the buffer container and the [bowl] *reservoir* and the microprocessor communicates with the automated valve.

5. The station of claim 1 wherein the disinfectant is bleach.

6. The station of claim 1 wherein the waste fluid source is a cart featuring a container having a drain connector that removably connects to the transfer connector of the station so that when said transfer pump is activated, and the cart drain and station transfer connectors are connected, waste fluid in the cart container is transferred to the station [bowl] *reservoir*.

7. A system for collecting, treating and disposing of waste fluid comprising:

a) a waste fluid treating and disposing, station including;
- i) a housing having transfer and flushing connectors;
- ii) a [bowl] *tank* positioned within said housing;
- iii) a dispenser containing a disinfectant;
- iv) a flushing pump having an inlet in communication with the disinfectant dispenser and an outlet selectively in communication with the [bowl] *tank* and the flushing connector;
- v) a transfer pump having an inlet in communication with the transfer connector and an outlet in communication with the [bowl] *tank*,
- vi) a mixing pump having an inlet and an outlet in communication with the [bowl] *tank* so that waste fluid therein is circulated;
- vii) a pH sensor in communication with the [bowl] *tank* so that a pH level of the circulating waste fluid may be detected;
- viii) a container holding a supply of buffer;
- ix) means for delivering buffer to the circulating waste fluid when the pH sensor detects that the pH level of the circulating waste fluid is above a predetermined pH level; and
- x) a microprocessor in communication with the pH sensor and in communication with and controlling the means for delivering buffer, the flushing pump, the transfer pump and the mixing pump.

8. The system for collecting, treating and disposing of waste fluid of claim 7 further comprising:

b) a waste fluid collection cart including:
- i) a body supported by a plurality of wheels;
- ii) a container supported by said body and featuring vacuum, suction, flushing and drain ports, where liquid waste is collected within the container through the suction port when the vacuum port is connected to a vacuum source and the flushing and drain ports are closed;
- iii) said drain port of the cart container removably connected to the transfer connector of the station so that waste fluid from the cart container is transferred to the station [bowl] *tank* when the transfer pump is activated; and
- iv) said flushing port of the cart container removably connected to the flushing connector of the station so that disinfectant may be directed to the cart container when the flushing pump is activated.

9. The system for collecting, treating and disposing of waste fluid of claim 7 further comprising a wash head positioned in the [bowl] *tank* and selectively in communication with the outlet of the flushing pump.

10. The system for collecting, treating and disposing of waste fluid of claim 7 wherein the disinfectant is bleach.

11. The system for collecting, treating and disposing of waste fluid of claim 7 wherein said [bowl] *tank* also communicates with a drain system.

12. The system for collecting, treating and disposing of waste fluid of claim 11 wherein the drain system includes drain pipe adapted to communicate with a sewer system and an eductor in communication with the drain pipe, said eductor including a venturi adapted to communicate with a water source so that water flows through the venturi which results in suction being applied to the drain pipe to aid in draining treated waste fluid from the station [bowl] *tank*.

13. The system for collecting, treating and disposing of waste fluid of claim 7 wherein the inlet of said flushing pump also is adapted to communicate with a source of water so that a mixture of disinfectant and water may selectively be delivered to the [bowl] *tank* and the flushing connector.

14. A station for treating waste fluid including:

a) a housing;

b) a [bowl] *reservoir* positioned within said housing and adapted to receive the waste fluid from a source and communicate with a drain system;

c) a mixing pump having an inlet and an outlet in communication with the [bowl] *reservoir* so that waste fluid therein is circulated;

d) a pH sensor in communication with the [bowl] *reservoir* so that a pH level of the circulating waste fluid may be detected;

e) a container holding a supply of buffer;

f) a pH controller in circuit between the buffer container and the [bowl] *reservoir* so that said pH controller controls the delivery of buffer to the circulating waste fluid;

g) said pH controller communicating with the pH sensor so that said pH controller delivers buffer to the circulating waste fluid when the pH sensor detects that the pH level of the circulating waste fluid is above a predetermined pH level;

h) a wash head positioned in the [bowl] *reservoir*;

i) a dispenser containing a disinfectant;

j) a flushing pump having an inlet in communication with a the disinfectant dispenser and an outlet in communication with the wash head so that when said flushing pump is activated, disinfectant is delivered to the contents of the [bowl] *reservoir*;

k) a transfer pump having an inlet in communication with a transfer connector and an outlet in communication with the [bowl] *reservoir*, said transfer connector adapted to communicate with the waste fluid source so that when said transfer pump is activated, waste fluid is transferred from the waste fluid source to the [bowl] *reservoir*; and l) a microprocessor in communication with the pH sensor and in communication with and controlling the pH controller, mixing pump, flushing pump and transfer pump m) said microprocessor programmed to perform the steps of:
- i. adding disinfectant to the collected waste fluid to create a solution;
- ii. mixing the solution;
- iii. allowing the solution to sit for a predetermined period of time;
- iv resuming mixing of the solution;
- v. detecting a pH level of the solution during the resumed mixing; and
- vi. adding a buffer to the solution during the resumed mixing until the pH levels drops below a predetermined level so that a treated solution is created.

*15. A system for handling waste fluid from a patient, comprising:*

*a) a movable waste fluid collection cart including:*

*i) a body supported by a plurality of wheels;*

*ii) a flushing portion and a drain portion; and*

*iii) at least two containers supported by the body, each container including a suction port, each container being configured to collect liquid waste from the patient via its respective suction port when a vacuum is applied to the container, at least one of the suction ports being configured to provide at least two different levels of suction, an outlet from each container being operatively connectable to the drain portion and an inlet to each container being operatively connectable to the flushing portion; and*

*b) a waste fluid disposal unit including:*

*i) a first portion coupleable to the flushing portion of the waste fluid collection cart, the first portion being connectable to a water source via a water line to provide water to the waste fluid collection cart when the first portion is coupled to the flushing portion; and*

*ii) a second portion coupleable to the drain portion of the waste fluid collection cart, the second portion being connectable to a drain via a drain pump, wherein patient's waste fluid in the waste fluid collection cart is pumpable to the drain by the drain pump when the second portion is coupled to the drain portion and to the drain.*

*16. The system of claim 15, wherein the waste fluid disposal unit further comprises a flushing pump between the water source and the first portion to pump water to the at least two containers when the first portion is coupled to the flushing portion.*

*17. The system of claim 15, wherein a level of vacuum in one of the at least two containers is controllable independently from a level of vacuum in another of the at least two containers.*

*18. The system of claim 15, further comprising a cleaning nozzle disposed in at least one of the containers, the cleaning nozzle in communication with the flushing portion to spray fluid into the at least one container.*

*19. The system of claim 18, wherein the moveable waste fluid collection cart comprises no more than first and second containers, first and second cleaning nozzles being disposed in the first and second containers respectively.*

*20. The system of claim 15, wherein the movable waste fluid collection cart further comprises a vacuum port for communicating with a vacuum system, and communicating with the suction ports of the containers so as to permit a vacuum to be pulled in the containers when the vacuum port is coupled to the vacuum system.*

*21. The system of claim 20, wherein the vacuum port is couplable to a vacuum system external to the movable waste fluid collection cart.*

*22. The system of claim 20, further comprising a vacuum control system comprising a plurality of valves in a vacuum network between the vacuum port and the suction ports of the containers, the valves being controllable by a user from a valve control panel.*

*23. The system of claim 22, wherein the plurality of valves comprises at least a first check valve on a vacuum path between the vacuum port and the first container and a second check valve on a vacuum path between the vacuum port and the second container.*

*24. The system of claim 15, further comprising a smoke filter disposed to filter smoke entering one of the containers from the patient.*

*25. The system of claim 15, wherein the flushing portion comprises a first flushing coupling operatively coupled to a first container of the at least two containers and a second flushing coupling operatively coupled to a second container of the at least two containers, the first and second flushing couplings being connectable to respective first and second connectors of the first portion of the waste fluid disposal unit.*

*26. The system of claim 15, wherein the drain portion comprises a first drain coupling operatively coupled to a first container of the at least two containers and a second drain coupling operatively coupled to a second container of the at least two containers, the first and second drain couplings being connectable to respective first and second connectors of the second portion of the waste fluid disposal unit.*

*27. The system of claim 15, wherein the waste fluid disposal unit further comprises a reservoir for containing treating liquid in fluid communication with the water line for injecting the treating fluid into the container when the first portion is coupled to the flushing portion.*

*28. The system of claim 15, wherein the at least two containers comprises only first and second containers.*

*29. A system for handling waste fluid from a patient, comprising:*

*a) a movable waste fluid collection cart including:*

*i) a body supported by a plurality of wheels;*

*ii) a flushing portion and a drain portion; and*

*iii) at least two containers supported by the body, each container including a suction port, each container being configured to collect liquid waste from the patient via its respective suction port when a vacuum is applied to the container, a level of suction at one of the suction ports being independently adjustable of a level of suction at another of the suction ports, outlets from the at least two containers being operatively connectable to the drain portion and an inlet to each container being operatively connectable to the flushing portion; and*

*b) a waste fluid disposal unit including:*

*i) a first portion coupleable to the flushing portion of the waste fluid collection cart, the first portion being connectable to a water source via a water line to provide water to the waste fluid collection cart when the first portion is coupled to the flushing portion;*

*ii) a second portion coupleable to the drain portion of the waste fluid collection cart, the second portion being connectable to a drain via a drain pump, wherein patient's waste fluid in the container is pumpable to the drain by the drain pump when the second portion is coupled to the drain portion and to the drain.*

*30. The system of claim 29, wherein the waste fluid disposal unit further comprises a reservoir for containing treating liquid in fluid communication with the water line for injecting the treating fluid into the container when the first portion is coupled to the flushing portion.*

*31. The system of claim 29, wherein the waste fluid disposal unit further comprises a flushing pump between the water source and the first portion to pump water into the container when the first portion is coupled to the flushing portion.*

*32. The system of claim 29, wherein at least one of the suction ports is configured to provide at least two different levels of suction.*

*33. The system of claim 29, further comprising a cleaning nozzle disposed in at least one of the containers, the cleaning nozzle in communication with the flushing portion to spray fluid into the at least one container.*

*34. The system of claim 33, wherein the moveable waste fluid collection cart comprises no more than first and second containers, first and second cleaning nozzles being disposed in the first and second containers respectively.*

*35. The system of claim 29, wherein the movable waste fluid collection cart including further comprises a vacuum port for communicating with a vacuum system, and communicating with the suction ports of the containers so as to permit a vacuum to be pulled in the containers when the vacuum port is coupled to the vacuum system.*

*36. The system of claim 35, wherein the vacuum port is couplable to a vacuum system external to the movable waste fluid collection cart.*

*37. The system of claim 35, further comprising a vacuum control system comprising a plurality of valves in a vacuum network between the vacuum port and the suction ports of the containers, the valves being controllable by a user from a valve control panel.*

*38. The system of claim 37, wherein the plurality of valves comprises at least a first check valve on a vacuum path between the vacuum port and the first container and a second check valve on a vacuum path between the vacuum port and the second container.*

*39. The system of claim 29, further comprising a smoke filter disposed to filter smoke entering one of the containers from a patient.*

*40. The system of claim 29, wherein the flushing portion comprises a first flushing coupling operatively coupled to a first container of the at least two containers and a second flushing coupling operatively coupled to a second container of the at least two containers, the first and second flushing couplings being connectable to respective first and second connectors of the first portion of the waste fluid disposal unit.*

*41. The system of claim 29, wherein the drain portion comprises a first drain coupling operatively coupled to a first container of the at least two containers and a second drain coupling operatively coupled to a second container of the at least two containers, the first and second drain couplings being connectable to respective first and second connectors of the second portion of the waste fluid disposal unit.*

* * * * *

UNITED STATES PATENT AND TRADEMARK OFFICE

CERTIFICATE OF CORRECTION

PATENT NO. : RE44,920 E
APPLICATION NO. : 13/772686
DATED : June 3, 2014
INVENTOR(S) : James L. Dunn and Lawrence E. Guerra It is certified that error appears in the above-identified patent and that said Letters Patent is hereby corrected as shown below:

On the Title Page:
Item No. (63): after "7,258,711", insert --, which is a Divisional of application No. 10/090,221, filed on Mar. 4, 2002, now Pat. No. 6,893,425.--

In the Specification:
Column 1
Line 15, after "7,258,711", insert --, which is a Divisional of application No. 10/090,221, filed on Mar. 4, 2002, now Pat. No. 6,893,425.--

Signed and Sealed this
Twenty-eighth Day of April, 2015

Michelle K. Lee

Michelle K. Lee
*Director of the United States Patent and Trademark Office*